United States Patent
Rasmussen et al.

(10) Patent No.: US 10,182,298 B2
(45) Date of Patent: Jan. 15, 2019

(54) HEARING ASSISTANCE DEVICE COMPRISING AN INPUT TRANSDUCER SYSTEM

(71) Applicant: Oticon A/S, Smørum (DK)

(72) Inventors: Karsten Bo Rasmussen, Smørum (DK); Søren Stranne, Smørum (DK); Søren Laugesen, Smørum (DK)

(73) Assignee: OTICFON A/S, Smørum (DK)

(*) Notice: Subject to any disclaimer, the term of this patent is extended or adjusted under 35 U.S.C. 154(b) by 0 days.

(21) Appl. No.: 15/359,316

(22) Filed: Nov. 22, 2016

(65) Prior Publication Data
US 2017/0078803 A1 Mar. 16, 2017

Related U.S. Application Data

(62) Division of application No. 14/487,826, filed on Sep. 16, 2014, now Pat. No. 9,538,296.

(30) Foreign Application Priority Data

Sep. 17, 2013 (EP) ..................... 13184713

(51) Int. Cl.
H04R 25/00 (2006.01)
A61N 1/05 (2006.01)
A61N 1/36 (2006.01)

(52) U.S. Cl.
CPC ........... *H04R 25/405* (2013.01); *H04R 25/00* (2013.01); *H04R 25/407* (2013.01);
(Continued)

(58) Field of Classification Search
CPC .................... H04R 25/305; H04R 25/453; H04R 2225/55; H04R 25/552; H04R 2225/023;
(Continued)

(56) References Cited

U.S. PATENT DOCUMENTS

| 4,207,441 A | 6/1980 | Ricard et al. |
| 4,532,930 A | 8/1985 | Crosby et al. |

(Continued)

FOREIGN PATENT DOCUMENTS

| EP | 1326479 A2 * | 7/2003 | ............. H03G 9/005 |
| EP | 1326479 A2 | 7/2003 | |

(Continued)

OTHER PUBLICATIONS

Engebretson et al., "Properties of an adaptive feedback equalization algorithm," Journal of Rehabilitation Research and Development, vol. 30, No. 1, 1993, pp. 8-16.
(Continued)

*Primary Examiner* — Matthew Eason
*Assistant Examiner* — Julie X Dang
(74) *Attorney, Agent, or Firm* — Birch, Stewart, Kolasch & Birch, LLP

(57) ABSTRACT

The application relates to a hearing assistance device (HAD) comprising (a) an input transducer system comprising (a1) an audio input transducer (AIT), and (a2) a first supplementary input transducer (SIT1), (b) an output transducer (OT) for converting a processed output signal to a stimulus perceivable by said user as sound, and (c) a signal processing unit (SPU) operationally connected to said audio input transducer (AIT), to said first supplementary input transducer (SIT1), and to said output transducer (OT), said signal processing unit (SPU) being configured for processing said electric audio input signal, and said first supplementary electric input signal, and for providing said processed output signal. The audio input transducer (AIT) is adapted for being located in an ear of the user. In a NORMAL mode of operation, electric audio input signal is processed in the signal processing unit and the supplementary electric input signal(s) are used to control the processing.

20 Claims, 7 Drawing Sheets

(52) U.S. Cl.
CPC .......... *H04R 25/453* (2013.01); *A61N 1/0541* (2013.01); *A61N 1/36036* (2017.08); *H04R 2225/021* (2013.01); *H04R 2225/025* (2013.01); *H04R 2225/41* (2013.01); *H04S 2420/05* (2013.01)

(58) Field of Classification Search
CPC .............................. H04R 25/45; H04R 25/554; H04R 2225/025; H04R 2225/41
USPC .................................................. 381/315–318
See application file for complete search history.

(56) References Cited

U.S. PATENT DOCUMENTS

| | | | |
|---|---|---|---|
| 5,144,675 A | 9/1992 | Killion et al. | |
| 5,961,443 A | 10/1999 | Rastatter et al. | |
| 7,471,799 B2 | 12/2008 | Neumann et al. | |
| 7,925,031 B2 | 4/2011 | Elmedyb et al. | |
| 2002/0147580 A1 | 10/2002 | Mekuria et al. | |
| 2005/0069161 A1 | 3/2005 | Kaltenbach et al. | |
| 2007/0009122 A1* | 1/2007 | Hamacher | H04R 25/453 381/312 |
| 2007/0121978 A1* | 5/2007 | Jang | H04R 25/405 381/315 |
| 2008/0107292 A1 | 5/2008 | Kornagel | |
| 2010/0040248 A1 | 2/2010 | Shridhar et al. | |
| 2010/0150385 A1 | 6/2010 | Sporer | |
| 2011/0098551 A1* | 4/2011 | Zhang | H04R 25/30 600/409 |
| 2011/0176685 A1* | 7/2011 | Elmedyb | H04M 1/20 381/23.1 |
| 2011/0188685 A1 | 8/2011 | Sheikh | |
| 2012/0121095 A1 | 5/2012 | Popovski et al. | |
| 2012/0213393 A1* | 8/2012 | Foo | H04R 25/554 381/315 |
| 2013/0094657 A1* | 4/2013 | Brammer | G10K 11/178 381/71.6 |
| 2013/0243228 A1* | 9/2013 | Muller | H04R 25/554 381/315 |
| 2013/0259263 A1* | 10/2013 | Konchitsky | G10K 11/002 381/94.1 |
| 2015/0139468 A1* | 5/2015 | Feilner | H04R 25/505 381/370 |

FOREIGN PATENT DOCUMENTS

| | | | | |
|---|---|---|---|---|
| EP | 1448016 A1 * | 8/2004 | ............ | H04R 3/005 |
| EP | 1448016 A1 | 8/2004 | | |
| EP | 1835785 A2 | 9/2007 | | |
| EP | 2088802 A1 * | 8/2009 | ........... | H04R 25/407 |
| EP | 2088802 A1 | 8/2009 | | |
| EP | 2124483 A2 | 11/2009 | | |
| EP | 2262285 A1 | 12/2010 | | |
| EP | 2581038 A1 * | 4/2013 | ............ | H04R 25/30 |
| EP | 2611218 A1 | 7/2013 | | |
| EP | 2611218 A1 * | 7/2013 | ........... | H04R 25/407 |
| EP | 1835785 A3 | 9/2013 | | |
| WO | WO 91/03042 A1 | 3/1991 | | |
| WO | WO 03/081947 A1 | 10/2003 | | |
| WO | WO 2007/137364 A1 | 12/2007 | | |

OTHER PUBLICATIONS

Extended European Search Report for European Application No. 13184713.9, dated Jan. 20, 2014.

Kjems et al., "Maximum likelihood based noise covariance matrix estimation for multi-microphone speech enhancement," 20th European Signal Processing Conference (EUSIPCO 2012), Bucharest, Romania, Aug. 27-31, 2012, pp. 295-299.

\* cited by examiner

HEARING ASSISTANCE DEVICE COMPRISING AN INPUT TRANSDUCER SYSTEM

This application is a Divisional of copending application Ser. No. 14/487,826, filed on Sep. 16, 2014, which claims priority under 35 U.S.C. § 119(a) to Application No. EP 13184713.9, filed in Europe on Sep. 17, 2013, all of which are hereby expressly incorporated by reference into the present application.

TECHNICAL FIELD

The present application relates to a hearing assistance device, e.g. a hearing instrument, adapted to be arranged at least partly on a user's head or at least partly implanted in a user's head, the hearing assistance device comprising an audio input transducer adapted for being located at or in an ear of a user.

Embodiments of the disclosure may e.g. be useful in applications such as hearing aids (e.g. air conduction hearing devices, bone anchored hearing devices, or cochlear implant hearing devices, or combinations thereof), headsets, ear phones, active ear protection systems, and combinations thereof.

BACKGROUND

The following account of the prior art relates to one of the areas of application of the present application, hearing instruments.

A hearing instrument providing the best sound quality experience will usually have a microphone at the entrance to the ear canal. This microphone location ensures that the naturally occurring information in the sound can be preserved—i.e. frequency spectrum, directional cues, interaural time difference, etc. At the same time, the implementation of a directional microphone system necessitates using microphones spaced some distance apart, typically 1 cm. A directional system offers the advantages of adaptive directionality contributing to the separation of wanted from unwanted sounds as long as they are emitted from different locations in space and in different directions (as seen from the hearing instrument). However, a directional system is known to disturb the basic sound quality of the signal-frequency colorations, phase changes and an increase in system noise are introduced by the directional system.

Using a microphone in or at the entrance to the ear canal is accepted in small hearing instruments such as completely in the canal (CIC) hearing instruments. It is well known, that such small hearing instruments have a limited amplification before acoustic feedback occurs and that the ventilation channel must also be of limited diameter such as less than perhaps 2 millimeters, depending on the hearing loss and on the use of a digital feedback cancellation system. A vent of only limited diameter may, however, cause occlusion problems for a substantial number of users.

Hearing instruments with one or more microphones located behind the pinna are often used in combination with a larger vent due to the limited risk of feedback with this more distant microphone location (distant from the speaker outlet). This microphone position behind the pinna does, however, limit the natural sound quality since the influence of the pinna on the sound is largely ignored.

US2010150385A1 deals with feedback prevention by arranging a directional microphone comprising two electrically interconnected microphones, and a receiver along a straight line. The directional effect of the directional microphone is set such that, when viewed from the directional microphone, the receiver is arranged in the direction of the lowest sensitivity of the directional microphone.

US2008107292A1 deals with an optically unnoticeable and acoustically improved behind-the-ear hearing device having a housing which can be worn behind the ear, a signal processing facility which is arranged in the housing, and which comprises an optoelectrical converter. Further, at least one optical microphone—arranged outside the housing—and connected to the signal processing facility by way of an optical wave guide is provided. The optical microphone can be positioned in the concha or in the auditory canal.

U.S. Pat. No. 7,471,799B2 deals with a method of noise reduction in a hearing aid or a listening device to be used by a hearing impaired person in which the noise reduction is provided primarily in the frequency range wherein the hearing impaired has the smallest hearing loss or the best hearing. Preferably, the noise reduction is achieved through beamforming of the signals from some or all of the microphones and whereby the number of microphones and their spacing is such that the highest directivity is provided in the frequency range, wherein the hearing impaired has the smallest hearing loss.

SUMMARY

An object of the present application is provide an improved hearing assistance device.

Objects of the application are achieved by the invention described in the accompanying claims and as described in the following.

A hearing assistance device:

In an aspect of the present application, an object of the application is achieved by a hearing assistance device (HAD) adapted for being arranged at least partly on a user's (U) head or at least partly implanted in a user's (U) head, the hearing assistance device comprising an input transducer system comprising
    an audio input transducer (AIT) for picking up a sound signal from the environment and providing an electric audio input signal,
    a first supplementary input transducer (SIT1) for picking up a sound signal from the environment and providing a first supplementary electric input signal,
an output transducer (OT) for converting a processed output signal to a stimulus perceivable by said user as sound, and
a signal processing unit (SPU) operationally connected to said audio input transducer (AIT), to said first supplementary input transducer (SIT1), and to said output transducer (OT), said signal processing unit (SPU) being configured for processing said electric audio input signal, and said first supplementary electric input signal, and for providing said processed output signal.

The audio input transducer (AIT) is adapted for being located in an ear of said user.

An advantage of the disclosure is that a hearing assistance device with good sound quality as well as directionality properties can be provided.

The present disclosure solves the conflicting demands of good sound quality and good directionality by combining one or more supplementary input transducers (e.g. supplementary microphones), e.g. located in a shell or housing of a BTE (Behind-The-Ear) hearing assistance device while introducing an audio input transducer (e.g. an audio microphone) in pinna, e.g. at the entrance to the ear canal. The audio input transducer is preferably the main input transducer and the signal coming from it treated according to control signals originating from the supplementary input transducer(s).

According to the present disclosure, it is proposed to locate one of the input transducers (termed the audio transducer, e.g. a microphone) in the ear (e.g. at the entrance to the ear canal). A position at the ear canal offers excellent sound quality but somewhat limited level of amplification—i.e. roughly 20 dB less amplification before feedback for a given vent size compared to a microphone position behind the ear. In an aspect, the (supplementary) input transducer(s) (e.g. microphones)—e.g. located behind the ear—can be used for additional amplification of the audio signal. Hence, the acoustic signal picked up behind the pinna may be amplified much more (perhaps 20 dB more) due to the increased distance between output and input transducer. According to this aspect, the key feature is to apply the highest amplification from (supplementary) input microphones e.g. located behind the pinna, while striving for a sound experience related to the signal picked up by the (audio) input transducer located in or around the entrance to the ear canal. This is done by exploiting what is known as the "law of the first wavefront" in room acoustics. Hence, it is well established that a suitably delayed signal may support speech intelligibility of the first arriving signal without being perceived as a separate signal. It is proposed to delay the signal from the (supplementary) input transducers somewhere between 1 and 20 milliseconds in order to exploit this effect. The size of the delay may be determined by the best compromise between sound quality aspects such as perceived acoustic echo and the correct perception of directionality of the sound. The highest needed amplification for the specific hearing instrument user may also play a part in the preferred delay. The "law of the first wavefront" is believed to be most useful for delays roughly in the range 1 to 20 milliseconds. A long delay may result in sound quality degradation such as a perceived echo, whereas a short delay may result in degradation of the directional information experienced by the hearing instrument user, i.e. the sound is not perceived as coming from the correct direction or no clear sense of direction is experienced.

In general, the hearing assistance device may contain any number of audio input transducers (where an audio transducer is (adapted for being) located in an ear of the user). In the present disclosure, only one is mentioned, though. In an embodiment, the hearing assistance contains one audio input transducer.

In general the supplementary input transducers (e.g. microphone(s)) can be (adapted to be) located anywhere on a user's body. Preferably, however, it/they is/are (adapted to be) located at a place on the user's body that is attractive from a sound reception point of view, e.g. on the user's head. In an embodiment, the hearing assistance device comprises a front (supplementary) input transducer microphone located in a forward facing part of the user's body and a rear (supplementary) microphone located in a backwards facing part of the user's body, whereby sound sources located in front of and to the rear of the user can be effectively separated (by means of the user's body).

In an embodiment, the hearing assistance device is configured to operate in different modes, e.g. at least two modes, such as at least three modes, or four or more modes. A 'mode of operation' at last partly determines the processing of the electric audio input signal and the supplementary electric input signal(s) by the signal processing unit. In an embodiment, the hearing assistance device is configured to operate in a normal (or default) mode, in a directional mode, or in a feedback mode.

In an embodiment, the signal processing unit is configured to provide that said processed output signal—in a normal mode of operation of the hearing assistance device—originates from (is a processed version of) said electric audio input signal.

In an embodiment, the hearing assistance device comprises a body-worn (BW) part adapted for being located at said user. In an embodiment, the BW-part comprises said first (and optionally one or more further) input transducer. In an embodiment, BW-part comprises said signal processing unit.

In an embodiment, the hearing assistance device comprises an implanted part. In an embodiment, the implanted part comprises a cochlear implant comprising an electrode for electrically stimulating a hearing nerve.

In an embodiment, the hearing assistance device comprises a partly implanted part. In an embodiment, the partly implanted part comprises a fixture implanted into the skull bone for supporting an external vibrator of a bone anchored (or bone-conduction) hearing assistance device.

The term 'located in an ear of a user' is in the present context taken to mean located on the front side of pinna, e.g. located in the conchae, such as in cymba (at the narrowest end of the conchae), or at the entrance to the ear canal, or in the ear canal.

In an embodiment, the audio input transducer is located in the conchae, such as in cymba located in the narrowest end of the conchae, or at the entrance to the ear canal, or in the ear canal.

In an embodiment, the hearing assistance device comprises an ITE part adapted for being located at least partly in an ear canal of the user.

In an embodiment, the BW-part and the ITE-part are two separate bodies. In an embodiment, a connecting element provides at least mechanical connection (e.g. an acoustic propagation element, e.g. a tube) and possibly electric connection between the two parts. In an embodiment, the body-worn (BW) part comprises (or is constituted by) a behind-the-ear (BTE) part adapted for being worn behind an ear (pinna) of the user. In an embodiment, the first and second supplementary microphones are located on the top of the BTE-part, whereby the sounds from front and rear directions relative to the user can be received by the microphones.

In an embodiment, the hearing assistance device comprises a communication interface allowing the audio microphone to be operatively (e.g. electrically) connected to the signal processing unit. In an embodiment, the hearing assistance device comprises a wireless link allowing the various functional parts, including the input and output transducers and the signal processing unit (e.g. located in a BW-part (e.g. a BTE-part) and/or in an ITE-part) to be in communication (including to exchange data). In an embodiment, the BW-part and the ITE-part are electrically connected via one or more electrical conductors extending between them.

In an embodiment, the output transducer comprises a receiver for converting said output signal to an acoustic sound signal. In an embodiment, the output transducer comprises a vibrator of a bone anchored hearing assistance device. In an embodiment, the output transducer comprises one or more electrodes of a cochlear implant hearing assistance device.

In an embodiment, the output transducer (e.g. a receiver) forms part of an open fitting (e.g. comprising a dome or a mould with a large vent) or a (semi) closed fitting (e.g. comprising an earpiece).

In an embodiment, the audio input transducer is located in an ITE-part of the hearing assistance device, where the ITE-part is adapted for being located at least partially in an ear canal of the user. In an embodiment, the ITE-part comprises a housing enclosing the audio input transducer (e.g. a microphone, the housing comprising an appropriate input transducer inlet opening). In an embodiment, the ITE part comprises the output transducer. In an embodiment, the housing comprises the output transducer (e.g. a receiver/loudspeaker, the housing comprising an appropriate output transducer outlet opening). In an embodiment, the ITE-part is configured to establish an electrical connection to another part of the hearing assistance device. In an embodiment, the ITE-part comprises an antenna and transceiver circuitry for establishing a wireless link to another part of the hearing assistance device (e.g. to a BW-part, such as to a BTE-part).

In an embodiment, the signal processing unit is located in a BTE-part. Alternatively, the signal processing unit (or a part thereof) may be located in the ITE-part or in an auxiliary device in communication with the BTE and/or ITE part. In an embodiment, the auxiliary device is or comprises a telephone, e.g. a SmartPhone. In an embodiment, the BTE-part comprises an antenna and transceiver circuitry for establishing a wireless link to another part of the hearing assistance device (e.g. the ITE part) and/or to another device, e.g. a SmartPhone.

In an embodiment, the hearing assistance device comprises a time to time-frequency conversion unit allowing a signal to be processed or analyzed at different frequencies, such as in a number of frequency bands.

In an embodiment, frequency bands dominated by unwanted sounds are identified by the supplementary input transducer(s) (e.g. microphone(s)), and a resulting supplementary control signal is used in the processing of the audio microphone signal. In an embodiment, detection of wind noise, or own voice, or other similar characteristics of the sound field around the hearing assistance device, based upon the signals picked up by the supplementary input transducer(s) (and possibly other detectors) may in a similar manner be used to influence the processing of the audio input transducer (e.g. microphone) signal.

In an embodiment, the hearing assistance device comprises one or more detectors of the acoustic environment of the hearing assistance device.

In an embodiment, the hearing assistance device comprises a level detector (LD) for determining the level of an input signal (e.g. on a band level and/or of the full (wide band) signal). The input level of the electric microphone signal picked up from the user's acoustic environment is e.g. a classifier of the environment.

In a particular embodiment, the hearing assistance device comprises a voice detector (VD or VAD (voice activity detector)) for determining whether or not an input signal comprises a voice signal (at a given point in time). A voice signal is in the present context taken to include a speech signal from a human being. It may also include other forms of utterances generated by the human speech system (e.g. singing). In an embodiment, the voice detector unit is adapted to classify a current acoustic environment of the user as a VOICE or NO-VOICE environment. This has the advantage that time segments of the electric microphone signal comprising human utterances (e.g. speech) in the user's environment can be identified, and thus separated from time segments only comprising other sound sources (e.g. artificially generated noise).

In an embodiment, the hearing assistance device comprises an own voice detector for detecting whether a given input sound (e.g. a voice) originates from the voice of the user of the system.

In an embodiment, the hearing assistance device comprises a wind noise detector and/or an own voice detector. In an embodiment, the hearing assistance device comprises a signal to noise ratio estimator (e.g. on a time frequency unit basis). In an embodiment, the hearing assistance device comprises a feedback detector. In an embodiment, the hearing assistance device comprises a detector of autocorrelation of a signal of the forward path. In an embodiment, the hearing assistance device comprises a detector of cross-correlation of two signals of the forward path.

In an embodiment, the at least one of the supplementary input transducer(s) form part of said one or more detectors.

A supplementary input transducer may e.g. be configured to identify noise in the environment, e.g. noise in one or more frequency ranges. In an embodiment, the hearing assistance device (e.g. the signal processing unit) is configured to reduce gain in the processing of the audio input signal when only noise is present and to increase gain when speech (and noise) is present. A supplementary input transducer may e.g. be configured to identify wind noise (e.g. using a cross-correlation detector, or the like). In an embodiment, the hearing assistance device (e.g. the signal processing unit) is configured to remove (or attenuate) such low-frequency noise in the audio input signal. A supplementary input transducer may e.g. be configured to identify a user's own voice. In an embodiment, the hearing assistance device (e.g. the signal processing unit) is configured to control the processing of the audio input signal, e.g. its volume (decrease during 'own voice').

Time Frequency Masking may be based on the supplementary input transducer(s) (e.g. a microphone pair) and imposed on the signal from the audio microphone. In addition, the signal (or a part thereof, e.g. one or more frequency bands) from one input transducer or from a weighted combination of several supplementary input transducers may—in a particular feedback mode of operation—be used as the audio signal in case of howling due to feedback problems in the hearing assistance device. In addition, the signal from one or more supplementary input transducers may be combined (e.g. linearly combined) with the signal from the audio input transducer signal into a directional system for improved directionality. A longer distance between input transducers (e.g. microphones) creates the possibility of increasing the directionality at low frequencies. A directional system comprising three input transducers may e.g. be combined into a system allowing to filter out noise in the horizontal plane or in the vertical plane. An increased risk of feedback is e.g. experienced when a telephone apparatus is held near one of the input transducers (e.g. the audio input transducer) of the hearing assistance device. In response to such increased risk (e.g. either detected by a feedback detector for detecting howl (or estimating loop gain), or by a proximity detector for detecting the proximity of a telephone), a feedback mode of operation may preferably be entered by the hearing assistance device.

In an embodiment, the hearing assistance device comprises a weighting unit providing a directional output signal from a number of input signals wherein said number of input signals comprise said electric audio input signal and said first and optionally further supplementary electric input signals.

In an embodiment, the hearing assistance device comprises a howl detector for detecting the occurrence or build-up of feedback howl, and wherein the signal processing unit is configured to provide that said processed output signal—in a feedback mode of operation of the hearing assistance device where feedback howl build-up of feedback howl is detected—fully or partially originates from said first and optionally further supplementary electric input signals.

The electric input signals are preferably provided in digitized form (the digitized signal comprising sample values of an analogue input signal at regularly spaced, distinct time instances). In an embodiment, a time frame is defined, each time frame containing a predefined number of samples (cf. e.g. FIG. 4A). A hearing assistance device according to the present disclosure may e.g. comprise a multitude of time to time time-frequency conversion units (e.g. one for each input signal that is not otherwise provided in a time-frequency representation, cf. e.g. FIG. 10) to provide each input signal $X_i(k,m)$ (i=1, 2, . . . , N) in a number of frequency bands k and a number of time instances m (the entity (k,m) being defined by corresponding values of indices k and m being termed a TF-bin or DFT-bin or TF-unit, cf. e.g. FIG. 4B. The hearing assistance device comprises a signal processing unit that receives time-frequency representations of the input signals and provides a time-frequency representation of a resulting, output signal. The signal processing unit is configured to determine the content of a given time-frequency bin (k,m) of the enhanced signal from the contents of corresponding TF-bins of the time-frequency representations of one or more of the electric input signals according to a predefined scheme.

In an embodiment, the signal processing unit is configured to provide that said processed output signal is a mixture according to a predefined scheme of said electric audio input signal said first and optionally further supplementary electric input signals on a time frequency unit basis, and wherein the actual mixture is influenced by said detectors.

In an embodiment, the predefined scheme comprises a criterion resulting in the selection of the contents of a given time-frequency bin (k,m) of one of the respective electric input signals for being used in the corresponding time-frequency bins (k,m) of the processed signal.

In an embodiment, the predefined scheme comprises selecting the time frequency units having the largest signal to noise ratio (SNR) among corresponding time frequency units of the electric input signals. This has the advantage of removing the need to prefer one source over the other.

In an embodiment, the phase of the resulting enhanced signal is determined by the origin of the signal at a particular time (and frequency). In other words, the resulting enhanced signal comprises magnitude and phase from the input signal (or a time frequency unit of the input signal) that is selected at a given point in time (that fulfils the predetermined scheme). Alternatively, the phase of the resulting enhanced signal may be synthesized (e.g. randomized) or smoothed to avoid large changes in phase from time instance to time instance (and/or from frequency band to frequency band).

Preferably, the electric input signals $X_i$ provide different representations (e.g. picked up at different locations and/or by different transducer means) of the same sound field constituting the current acoustic environment of the hearing assistance device.

An electric input signal $X_i(k,m)$ (i=1, 2, . . . , N) may represent a signal from an input transducer, e.g. a microphone (e.g. a normal microphone or a vibration sensing bone conduction microphone), or an accelerometer, or a wireless receiver.

In an embodiment, the hearing assistance device comprises a beamformer, which provides spatial filtering of the noisy signal, and a single channel (SC) noise reduction filter, which reduces the noise remaining in the beamformer output. Such system (which is working in the time-frequency domain) is e.g. described by [Kjems and Jensen; 2012].

The audio microphone may e.g. be placed at the entrance of the ear canal or other attractive locations on the front side of pinna (as regards frequency spectrum, directional cues, interaural time differences, etc.), e.g. in the conchae, such as in the narrowest end of the conchae (cymba).

In an embodiment, each input transducer path comprises an amplifier unit configured to individually amplify respective electric input signals (e.g. controlled by the signal processing unit, e.g. according to a predefined or adaptive scheme). In an embodiment, the amplifier units are configured to apply a larger amplification to the supplementary electric input signals than to the electric audio input signal, e.g. larger than 10 dB or more, such as larger than 20 dB or more.

In an embodiment, at least one (such as all) of the supplementary input transducer paths comprises a delay unit for selectively applying delay to the respective electric input signals and providing respective delayed input signals. The delay unit(s) is/are operationally coupled to the supplementary input transducer (s) and to a weighting unit for mixing two or all of the input signals (e.g. providing a weighted sum, e.g. adding them (weights=1)) or selecting one of the inputs and providing a resulting input signal that is fed to processing unit for further enhancement (e.g. noise reduction, feedback suppression, etc.). Preferably, the delay applied by the delay unit(s) to the respective (amplified) input signal(s) from the (supplementary) input transducer(s) is preferably configured to be between 1 and 20 milliseconds. In an embodiment, the delay is larger than 1 ms. In an embodiment, the delay is smaller than 20 ms. In an embodiment, The delay is in the range between 2 and 15 ms, such as between 5 and 10 ms. In an embodiment, the delay is larger than 3 ms, such as larger than 5 ms. In an embodiment, the delay is smaller than 15 ms, such as smaller than 10 ms.

In an embodiment, the ITE-part comprises the signal processing unit. In an embodiment, the ITE-part is configured—in a specific autonomous mode of operation—to be operational with limited functionality. In an embodiment, the ITE-part alone is configured to operate as a normal hearing aid under normal conditions, e.g. where no or limited communication with other parts or devices is needed. In an embodiment, the ITE-part and the BW-part together provide enhanced functionality, e.g. connectivity to external devices.

In an embodiment, the hearing assistance device is adapted to provide a frequency dependent gain to compensate for a hearing loss of a user. Various aspects of digital hearing aids are described in [Schaub; 2008].

In an embodiment, the hearing assistance device comprises an antenna and transceiver circuitry for wirelessly receiving a direct electric input signal from (and/or transmitting an electric output signal to) another device, e.g. a communication device or another hearing assistance device.

Preferably, communication between the hearing assistance device and the other device (or between different parts of the hearing assistance device) is based on some sort of modulation at frequencies above 100 kHz. Preferably, frequencies used to establish a communication link between the hearing assistance device and the other device is below 50 GHz, e.g. located in a range from 50 MHz to 50 GHz, e.g. above 300 MHz, e.g. in an ISM range above 300 MHz, e.g. in the 900 MHz range or in the 2.4 GHz range or in the 5.8 GHz range or in the 60 GHz range (ISM=Industrial, Scientific and Medical, such standardized ranges being e.g. defined by the International Telecommunication Union, ITU). In an embodiment, the wireless link is based on a standardized or proprietary technology. In an embodiment, the wireless link is based on Bluetooth technology (e.g. Bluetooth Low-Energy technology). In an embodiment, the wireless link is based on near-field, e.g. capacitive or inductive communication.

In an embodiment, the hearing assistance device is portable device, e.g. a device comprising a local energy source, e.g. a battery, e.g. a rechargeable battery.

The hearing assistance device comprises a forward or signal path between an input transducer (microphone system and/or direct electric input (e.g. a wireless receiver)) and the output transducer. The signal processing unit is located in the forward path. In an embodiment, the signal processing unit is adapted to provide a frequency dependent gain according to a user's particular needs. In an embodiment, the hearing assistance device comprises an analysis path comprising functional components for analyzing the input signal (e.g. determining a level, a modulation, a type of signal, the presence of acoustic feedback, an acoustic feedback estimate, the presence of wind noise, a signal to noise ratio, etc.). In an embodiment, some or all signal processing of the analysis path and/or the signal path is conducted in the frequency domain. In an embodiment, some or all signal processing of the analysis path and/or the signal path is conducted in the time domain.

In an embodiment, the hearing assistance device comprises an acoustic (and/or mechanical) feedback suppression system. Acoustic feedback occurs because the output loudspeaker signal from an audio system providing amplification of a signal picked up by a microphone is partly returned to the microphone via an acoustic coupling ('feedback path') through the air or other media. The part of the loudspeaker signal returned to the microphone is then re-amplified by the system before it is re-presented at the loudspeaker, and again returned to the microphone. As this cycle continues, the effect of acoustic feedback becomes audible as artifacts or even worse, howling, when the system becomes unstable. The problem appears typically when the microphone and the loudspeaker are placed closely together, as e.g. in hearing aids or other audio systems. Adaptive feedback cancellation has the ability to track feedback path changes over time. It is also based on a linear time invariant filter to estimate the feedback path by updating the filter weights over time [Engebretson, 1993]. The filter update may be calculated using stochastic gradient algorithms, including some form of the Least Mean Square (LMS) or the Normalized LMS (NLMS) algorithms. They both have the property to minimize the error signal in the mean square sense with the NLMS additionally normalizing the filter update with respect to the squared Euclidean norm of some reference signal. Other adaptive algorithms (than LMS and NLMS) may be used depending on the particular application. Various aspects of adaptive filters are e.g. described in [Haykin].

In an embodiment, the hearing assistance device further comprises other relevant functionality for the application in question, e.g. compression, noise reduction, etc.

In an embodiment, the hearing assistance device comprises a listening device, e.g. a hearing aid, e.g. a hearing instrument, e.g. a hearing instrument adapted for being located at the ear or fully or partially in the ear canal of a user, e.g. a headset, an earphone, an ear protection device or a combination thereof.

Use:

In an aspect, use of a hearing assistance device as described above, in the 'detailed description of embodiments' and in the claims, is moreover provided. In an embodiment, use is provided in a system comprising a microphone and a loudspeaker in sufficiently close proximity of each other to cause feedback from the loudspeaker to the microphone during operation by a user. In an embodiment, use is provided in a system comprising one or more hearing instruments, headsets, ear phones, active ear protection systems, etc., e.g. in handsfree telephone systems, teleconferencing systems, public address systems, karaoke systems, classroom amplification systems, etc.

A Hearing Assistance System:

In a further aspect, a hearing assistance system comprising a hearing assistance device as described above, in the 'detailed description of embodiments', and in the claims, AND an auxiliary device is moreover provided.

In an embodiment, the system is adapted to establish a communication link between the hearing assistance device and the auxiliary device to provide that information (e.g. control and status signals, sensor/detector signals, possibly audio signals) can be exchanged or forwarded from one to the other.

In an embodiment, the auxiliary device is or comprises an audio gateway device adapted for receiving a multitude of audio signals (e.g. from an entertainment device, e.g. a TV or a music player, a telephone apparatus, e.g. a mobile telephone or a computer, e.g. a PC) and adapted for selecting and/or combining an appropriate one of the received audio signals (or combination of signals) for transmission to the hearing assistance device. In an embodiment, the auxiliary device is or comprises a remote control for controlling functionality and operation of the hearing assistance device(s). In an embodiment, the function of a remote control is implemented in a SmartPhone, the SmartPhone possibly running an APP allowing to control the functionality of the hearing assistance device via the SmartPhone (the hearing assistance device(s) comprising an appropriate wireless interface to the SmartPhone, e.g. based on Bluetooth or some other standardized or proprietary scheme). In an embodiment, the auxiliary device is or comprises a detector for influencing (or contributing to) the control of the input transducer system of the hearing assistance device. In an embodiment, the auxiliary device comprises a SmartPhone comprising said detector (and/or comprises user interface for the detector), the SmartPhone possibly running an APP allowing a user to influence the detector (e.g. by influencing a location or direction of measurement by the detector) and/or the control of the input transducer system of the hearing assistance device.

In an embodiment, the auxiliary device is another hearing assistance device. In an embodiment, the other hearing assistance device comprises a detector whose measurement result is used in the hearing assistance device to control of the input transducer system. In an embodiment, the hearing assistance system comprises two hearing assistance devices adapted to implement a binaural hearing assistance system, e.g. a binaural hearing aid system.

Definitions

In the present context, a 'hearing assistance device' refers to a device, such as e.g. a hearing instrument or an active ear-protection device or other audio processing device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears. A 'hearing assistance device' further refers to a device such as an earphone or a headset adapted to receive audio signals electronically, possibly modifying the audio signals and providing the possibly modified audio signals as audible signals to at least one of the user's ears. Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve of the user.

The hearing assistance device may be configured to be worn in any known way, e.g. as a unit arranged behind the ear with a tube leading radiated acoustic signals into the ear canal or with a loudspeaker arranged close to or in the ear canal, as a unit entirely or partly arranged in the pinna and/or in the ear canal, as a unit attached to a fixture implanted into the skull bone, as an entirely or partly implanted unit, etc. The hearing assistance device may comprise a single unit or several units communicating electronically with each other.

More generally, a hearing assistance device comprises an input transducer for receiving an acoustic signal from a user's surroundings and providing a corresponding input audio signal and/or a receiver for electronically (i.e. wired or wirelessly) receiving an input audio signal, a signal processing circuit for processing the input audio signal and an output means for providing an audible signal to the user in dependence on the processed audio signal. In some hearing assistance devices, an amplifier may constitute the signal processing circuit. In some hearing assistance devices, the output means may comprise an output transducer, such as e.g. a loudspeaker for providing an air-borne acoustic signal or a vibrator for providing a structure-borne or liquid-borne acoustic signal. In some hearing assistance devices, the output means may comprise one or more output electrodes for providing electric signals.

In some hearing assistance devices, the vibrator may be adapted to provide a structure-borne acoustic signal transcutaneously or percutaneously to the skull bone. In some hearing assistance devices, the vibrator may be implanted in the middle ear and/or in the inner ear. In some hearing assistance devices, the vibrator may be adapted to provide a structure-borne acoustic signal to a middle-ear bone and/or to the cochlea. In some hearing assistance devices, the vibrator may be adapted to provide a liquid-borne acoustic signal to the cochlear liquid, e.g. through the oval window. In some hearing assistance devices, the output electrodes may be implanted in the cochlea or on the inside of the skull bone and may be adapted to provide the electric signals to the hair cells of the cochlea, to one or more hearing nerves, to the auditory cortex and/or to other parts of the cerebral cortex.

A 'hearing assistance system' refers to a system comprising one or two hearing assistance devices, and a 'binaural hearing assistance system' refers to a system comprising one or two hearing assistance devices and being adapted to cooperatively provide audible signals to both of the user's ears. Hearing assistance systems or binaural hearing assistance systems may further comprise 'auxiliary devices', which communicate with the hearing assistance devices and affect and/or benefit from the function of the hearing assistance devices. Auxiliary devices may be e.g. remote controls, audio gateway devices, mobile phones, public-address systems, car audio systems or music players. Hearing assistance devices, hearing assistance systems or binaural hearing assistance systems may e.g. be used for compensating for a hearing-impaired person's loss of hearing capability, augmenting or protecting a normal-hearing person's hearing capability and/or conveying electronic audio signals to a person.

Further objects of the application are achieved by the embodiments defined in the dependent claims and in the detailed description of the invention.

As used herein, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element or intervening elements may be present, unless expressly stated otherwise. Furthermore, "connected" or "coupled" as used herein may include wirelessly connected or coupled. As used herein, the term "and/or" includes any and all combinations of one or more of the associated listed items. The steps of any method disclosed herein do not have to be performed in the exact order disclosed, unless expressly stated otherwise.

BRIEF DESCRIPTION OF DRAWINGS

The disclosure will be explained more fully below in connection with a preferred embodiment and with reference to the drawings in which.

The figures are schematic and simplified for clarity, and they just show details which are essential to the understanding of the disclosure, while other details are left out. Throughout, the same reference signs are used for identical or corresponding parts.

Figure 1A:
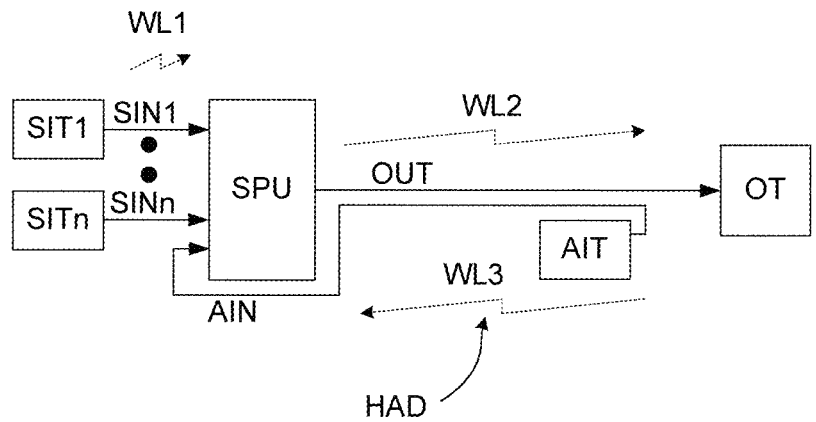
FIGS. 1A, 1B, 1C, 1D, 1E, and 1F show six embodiments of a hearing assistance device according to the present disclosure.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

FIG. 1 shows six embodiments of a hearing assistance device (HAD) according to the present disclosure. Each of the embodiments of a hearing assistance device (HAD) comprises an input transducer system for picking up a sound from the environment and providing a number of electric input signals. The input transducer system comprises an audio input transducer (AIT) for picking up a sound signal from the environment and providing an electric audio input signal (AIN). The audio input transducer (AIT) is adapted for being located in an ear of a user, e.g. near the entrance of an ear canal (e.g. at or in the ear canal or outside the ear canal but in the concha part of pinna. The aim of the location is to allow the audio input transducer to pick up sound signals that include the cues resulting from the function of pinna (e.g. directional cues). The input transducer system further comprises a first supplementary input transducer (SIT1) for picking up a sound signal from the environment and providing a first supplementary electric input signal (SIN1). The embodiment of FIG. 1A comprises n supplementary input transducers (SIT1, . . . , SITn). The number of input transducers n can be any of any size that make sense from a signal processing point of view (and may include input transducers of a mobile device, e.g. a SmartPhone or even fixedly installed input transducers in communication with the signal processing unit). Each input transducer of the embodiment of FIG. 1A provides respective supplementary electric input signals (SIN1, . . . , SINn), whereas the embodiments of FIG. 1B, 1C, 1D, 1E, 1F comprise two supplementary input transducers in the form of microphones (e.g. omni-directional microphones) (SIT1, SIT2). Each or the input transducers of the input transducer system can theoretically be of any kind, such as comprising a microphone (e.g. a normal microphone or a vibration sensing bone conduction microphone), or an accelerometer, or a wireless receiver. Each of the embodiments of a hearing assistance device (HAD) comprises an output transducer (OT) for converting a processed output signal to a stimulus perceivable by the user as sound. The output transducer may in general be located at any appropriate part on, or fully or partly inside the user's body. Preferably, the output transducer is located where its output stimuli are perceivable to the user. In the embodiments of FIG. FIG. 1B, 1C, 1D, 1E, 1F, the output transducer is shown as receivers (loudspeakers). A receiver can e.g. be located in an ear canal (RITE-type (Receiver-In-The-ear) or a CIC (completely in the ear canal-type) hearing assistance device) or outside the ear canal (e.g. a BTE-type hearing assistance device), e.g. coupled to a sound propagating element (e.g. a tube) for guiding the output sound from the receiver to the ear canal of the user (e.g. via an ear mould located at or in the ear canal). Alternatively, other output transducers can be envisioned, e.g. a vibrator of a bone anchored hearing assistance device, or a number electrodes of a cochlear implant hearing assistance device. The hearing assistance device further comprises a signal processing unit (SPU) operationally connected to the audio input transducer (AIT), to the first supplementary input transducers (SIT1, SIT2, . . . , SITn), and to the output transducer (OT). The 'operational connections' between the functional elements (signal processing unit (SPU), input transducers (AIT, SIT1, SIT2, . . . , SITn), and output transducer (OT)) of the hearing assistance device (HAD) can be implemented in any appropriate way allowing signals to the transferred (possibly exchanged) between the elements (at least to enable a forward path from the input transducers to the output transducer, via (and in control of) the signal processing unit). The solid lines (denoted AIN, SIN1, SIN2, . . . , SINn, OUT) represent wired electric connections. The dotted or dashed zig-zag lines (denoted WL1, WL2, WL3, WL in FIGS. 1A, 1B, 1C and 1F, respectively) represent alternative non-wired electric connections, e.g. wireless connections, e.g. based on electromagnetic signals, in which case the inclusion of relevant antenna and transceiver circuitry is implied). One or more of the wireless links may be based on Bluetooth technology (e.g. Bluetooth Low-Energy technology).

Thereby a large bandwidth and a relatively large transmission range is provided. Alternatively or additionally, one or more of the wireless links may be based on near-field, e.g. capacitive or inductive, communication. The latter has the advantage of having a low power consumption. The signal processing unit (SPU) is configured for processing the electric audio input signal AIN), and the supplementary electric input signals (SIN1, SIN2, . . . , SINn), and for providing a processed (preferably enhanced) output signal (OUT). The signal processing unit (SPU) may e.g. comprise a directional algorithm for providing an omni-directional signal or—in a particular DIR mode—a directional signal based on one or more of the electric input signals (AIN, SIN1, SIN2, . . . , SINn). The signal processing unit (SPU) may preferably comprise a noise reduction algorithm for— in a particular NORMAL mode—processing the electric audio input signal (AIN) to provide the processed output signal (OUT) based on information derived from the supplementary electric input signals (SIN1, SIN2, . . . , SINn). The signal processing unit (SPU) may e.g. comprise a feedback detector and be configured to—in a particular FEEDBACK mode where feedback above a predefined level is detected (e.g. in a particular frequency band or overall)—process a signal based on one or more of the supplementary electric input signals (SIN1, SIN2, . . . , SINn) to provide the processed output signal (OUT). All embodiments of a hearing assistance device are adapted for being arranged at least partly on a user's head or at least partly implanted in a user's head.

FIG. 1B to 1F are intended to illustrate different partitions of the hearing assistance device of FIG. 1A. The following brief discussion of FIG. 1B to 1E is thus focussed on this aspect. Otherwise, reference is made to the above general description.

Figure 1B:
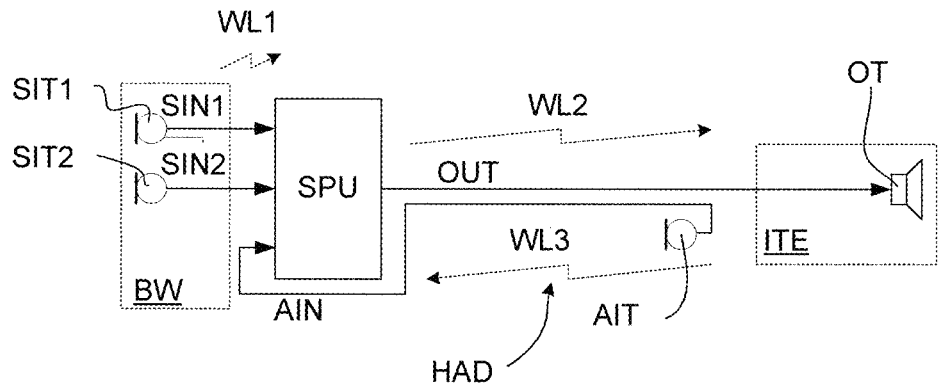

FIG. 1B shows an embodiment of a hearing assistance device as shown in FIG. 1A, but where it is specified that the (two) supplementary input transducers (SIT1, SIT2) are located in a separate first body-worn part (BW) adapted to be worn on the user's body. Preferably, the body-worn part is adapted to be located at a place on the user's body that is attractive from a sound reception point of view, e.g. on the user's head. The output transducer (OT) is located in an in-the-ear part (ITE) adapted for being located in the ear of a user, e.g. in the ear canal of the user, e.g. as is customary in a RITE-type hearing assistance device. The signal processing unit (SPU) may be located in the first body-worn part (BW) but may alternatively be located elsewhere, e.g. in a second body-worn part, e.g. in another hearing assistance device, in an audio gateway device, in a remote control device, and/or in a SmartPhone. The audio input transducer (AIT) may be located in the in-the-ear part (ITE) or elsewhere in the ear of the user, e.g. in concha, e.g. in the cymba-region.

Figure 1C:
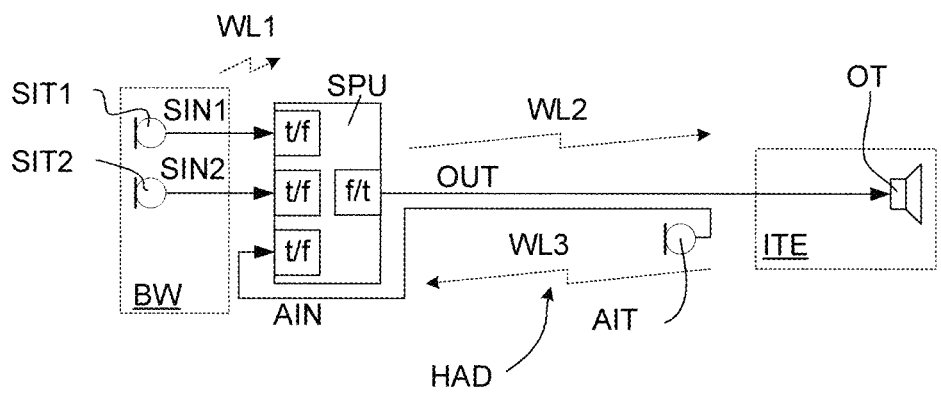

FIG. 1C shows an embodiment of a hearing assistance device (HAD) as shown in FIG. 1B, but including time-frequency conversion units (t/f) enabling analysis and/or processing of the electric input signals (AIN, SIN1, SIN2) from the input transducers (AIT, SIT1, SIT2) in the frequency domain. The time-frequency conversion units (t/f) are shown to be included in the signal processing unit (SPU), but may alternatively form part of the respective input transducers. The hearing assistance device further comprises a frequency to time transducer (f/t), shown to be included in the signal processing unit (SPU). Such functionality may alternatively be located elsewhere, e.g. in connection with the output transducer (OT). In the embodiment of FIG. 1C, time-frequency conversion units (t/f) are shown to be provided in all microphone paths. This need not be the case though. Only one of the microphone paths may be provided with such conversion units, e.g. the audio microphone path, or alternatively only (one, some or all of) the supplementary microphone paths. The location of the signal processing unit (SPU) and the audio input microphone (AIT) may be as discussed in connection with the embodiment of FIG. 1B.

Figure 1D:
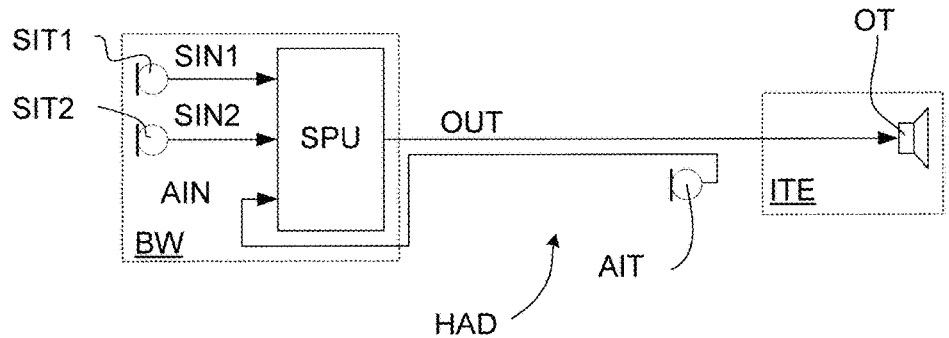

FIG. 1D shows an embodiment of a hearing assistance device (HAD) as shown in FIG. 1B or 1C, but the signal processing unit (SPU) is located in the body-worn part (BW) together with the supplementary input transducers (SIT1, SIT2). Again the location of the audio microphone is NOT specified, and may be located as discussed in connection with the embodiment of FIG. 1B.

Figure 1E:
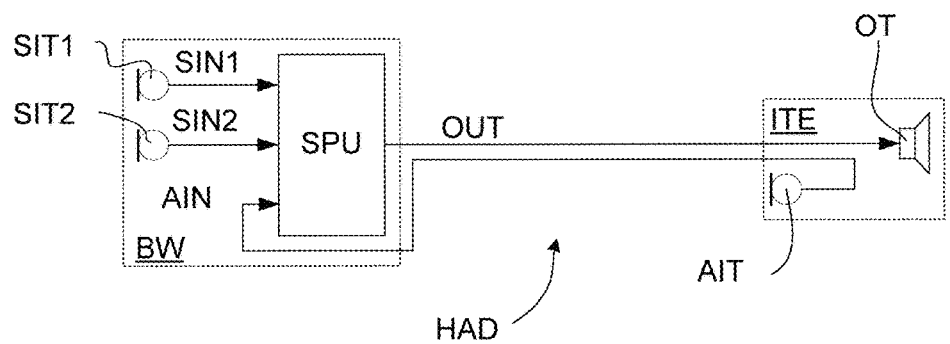

FIG. 1E shows an embodiment of a hearing assistance device (HAD) as shown in FIG. 1D, but where the audio microphone (AIT) is located in ITE-part (ITE) together with the output transducer (OT). This has the advantage that the BW-part (e.g. a BTE-part) and the ITE-part can be operatively connected by a single connecting element allowing appropriate electrical connection of the audio microphone (AIT) and the output transducer (OT of the ITE-part to the signal processing unit (SPU) of the BW-part.

Figure 1F:
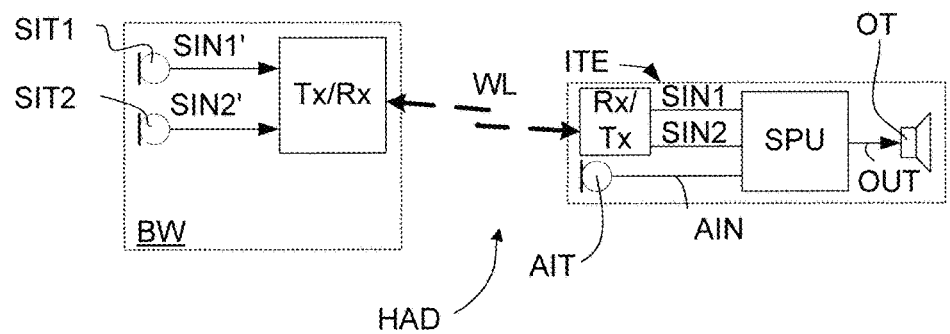

FIG. 1F illustrates an embodiment of a hearing assistance device (HAD), wherein the signal processing unit (SPU) is located in the ITE-part, and wherein the supplementary microphones (SIT1, SIT2) are located in the body worn part (BW) (e.g. a BTE-part) and connected to respective antenna and transceiver circuitry (together denoted Tx/Rx) for wirelessly transmitting the electric microphone signals SIN1' and SIN2' to the ITE-part via wireless link WL. The ITE-part comprises audio microphone (AIT) and antenna and transceiver circuitry (together denoted Rx/Tx) for receiving the wirelessly transmitted electric microphone signals SIN1' and SIN2' from the BW-part. The electric audio input signal AIN, and the supplementary electric input signals SIN1, SIN2 are connected to the signal processing unit (SPU), which processes the microphone signals and provides a processed output signal (OUT), which is forwarded to output transducer OT and converted to an output sound. The wireless link WL between the BW- and ITE-parts may be based on any appropriate wireless technology. In an embodiment, the wireless link is based on an inductive (near-field) communication link. In a first embodiment, the BW-part and the ITE-part may each constitute self-supporting (independent) hearing assistance devices. In second embodiment, the ITE-part may constitute self-supporting (independent) hearing assistance device, and the BW-part is an auxiliary device that is added to provide extra functionality. In an embodiment, the extra functionality may include one or more supplementary microphones of the BW-part to provide directionality and/or alternative audio input signal(s) to the ITE-part. In an embodiment, the extra functionality may include added connectivity, e.g. to provide wired or wireless connection to other devices, e.g. a partner microphone, a particular audio source (e.g. a telephone, a TV, or any other entertainment sound track).

FIG. 2 shows two embodiments of a hearing assistance device according to the present disclosure.

Figure 2A:
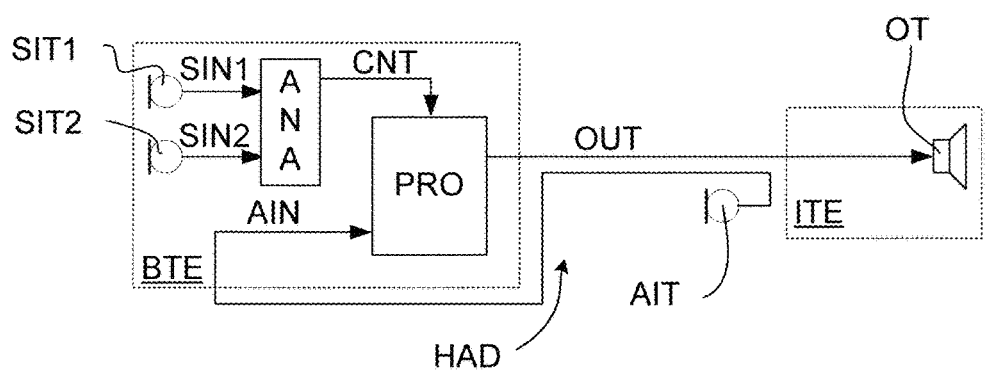
FIGS. 2A and 2B show two embodiments of a hearing assistance device according to the present disclosure.

FIG. 2A further illustrates an embodiment of a hearing assistance device (HAD) as shown in FIG. 1D, where the supplementary input transducers and the signal processing unit (SPU) are located in a body-worn unit (BW), e.g. a BTE-unit. The signal processing unit (SPU) of FIG. 1D comprises in the embodiment of FIG. 2A a processing unit (PRO) for processing an electric input signal and providing a processed output signal (OUT). The signal processing unit further comprises an analysis unit that analyses supplementary input signals SIN1, SIN2 an provides an output control signal CNT which is used by the processing unit (PRO) to influence or control the processing of electric audio input signal AIN. The signal from the audio input transducer (AIT) is thus used in forward path as a basis for the processed output signal (OUT), which is fed to the output transducer (OT). The audio input transducer (AIT) is NOT located in the ITE part, but implemented in another (e.g. self-contained) body, e.g. located in concha or separately from the ITE-part at the ear canal opening.

Figure 2B:
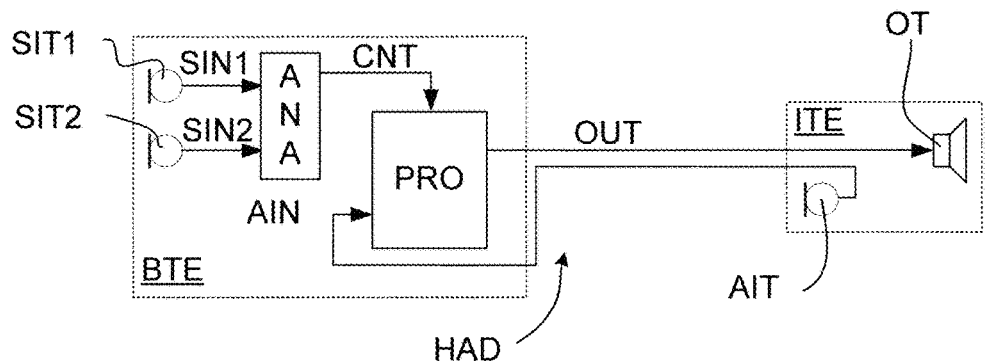

FIG. 2B shows an embodiment of a hearing assistance device (HAD) as shown in FIG. 2A but where the audio input transducer form part of ITE part (ITE). In an embodiment, the ITE-part is adapted to be located in the ear canal of the user so that the audio input transducer (AIT) is positioned near the opening of the ear canal. Alternatively, the ITE-part is adapted to be located deeper in the ear canal of the user, e.g. so that the audio input transducer (AIT) is positioned near the opening of the ear canal, such as withdrawn from the opening, i.e. in the ear canal.

FIG. 3 shows two embodiments of a hearing assistance device according to the present disclosure.

Figure 3A:
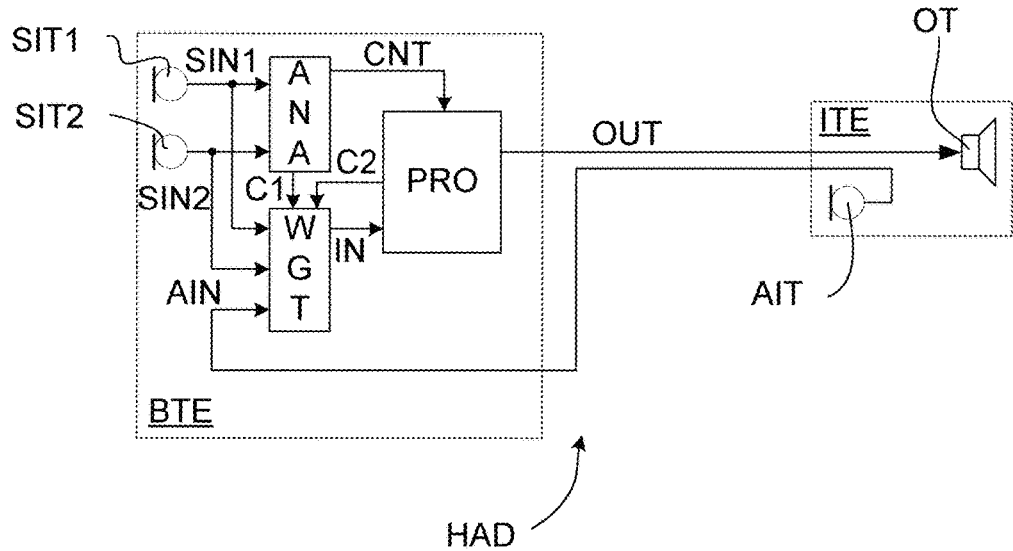
FIGS. 3A and 3B show two embodiments of a hearing assistance device according to the present disclosure, FIGS. 4A and 4B schematically show a conversion of a signal in the time domain to the time-frequency domain, FIG. 4A illustrating a time dependent sound signal (amplitude versus time) and its sampling in an analogue to digital converter, FIG. 4B illustrating a resulting 'map' of time-frequency units after a Fourier transformation of the sampled signal.

FIG. 3A shows an embodiment of a hearing assistance device, which in addition to the analysis unit (ANA) (for receiving and analysing the supplementary electric input signals (SIN1, SIN2) and providing a control signal to the processing unit (PRO)) comprises a weighting (mixing) unit (WGT) for generating a weighted combination of the electric input signals (SIN1, SIN2, AIN) from the supplementary input transducers (SIT1, SIT2) and the audio input transducer (AIT). The output of the weighting unit (WGT) is the resulting audio input signal (IN) that is processed by the processing unit (PRO) to provide the processed (audio) output signal (OUT). In an embodiment, the weighting unit (WGT) is controlled by control signals C1 and C2 from the analysis (ANA) and processing (PRO) units, respectively, to provide a directional output (IN) signal from two or all of the electric input signals (SIN1, SIN2, AIN). In an embodiment, the weighting of the electric input signals is performed on a time-frequency unit basis according to a predefined criterion (e.g. involving an assumption regarding properties of a target signal (e.g. its direction)). The use of a weighting function (a time-frequency mask) to provide a resulting (e.g. directional signal) from two or more microphone input signals available in a time-frequency representation is e.g. described in EP2088802A1. In an embodiment, the weighting unit (WGT) is controlled by control signals C1 and C2 to select one of the electric input signal as the resulting audio input signal (IN) or to fully exclude one of them from contributing to the resulting audio input signal (IN). Another implementation of a multi-microphone, beam forming and noise reduction system operating in the (time-)frequency domain is e.g. described by [Kjems and Jensen; 2012].

Figure 3B:
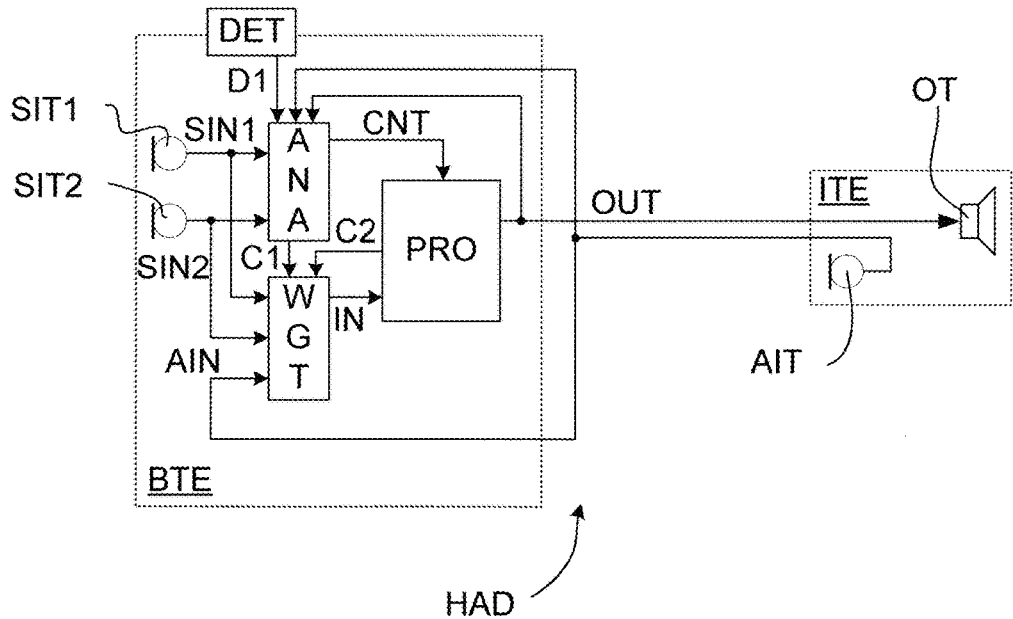

FIG. 3B shows an embodiment of a hearing assistance device as in FIG. 3A, but additionally comprising one or more detectors (DET) of the acoustic environment for influencing the analysis of supplementary signals and/or the weighting of electric input signals from the input transducers to provide the resulting audio input signal (IN) its processing in the processing unit (PRO) via control signals C1, C2 and CNT, respectively. Further, the electric audio input signal AIN and the processed (audio) output signal OUT are fed to the analysis unit (ANA) for analysis together with the detector signal(s) D1 and the supplementary electric input signals SIN1, SIN2 to provide control signal CNT and C1.

In an embodiment, the hearing assistance device (e.g. the analysis unit (ANA)) comprises a detector of wind noise. Such detector can e.g. be implemented by comparing the electric input signals of two or more of the input transducers, e.g. two supplementary input transducers SIT1, SIT2, e.g. microphones, e.g. omni-directional microphones), or alternatively a supplementary (e.g. SIT1) and the audio microphone (AIT). Wind noise detectors are known in the art. EP1448016A1 deals for example with a device for detecting the presence of wind noise in an array of microphones based on a comparison of auto correlation of one or each microphone signal, and cross correlation or the two microphone signals.

In an embodiment, the hearing assistance device (e.g. the analysis unit (ANA)) comprises a level detector for determining the level of an input signal (e.g. on a band level and/or of the full (wide band) signal). The input level of the electric input signal picked up from the user's acoustic environment is e.g. a classifier of the environment. Level detection in hearing aids is e.g. described in WO 03/081947 A1 or U.S. Pat. No. 5,144,675.

In an embodiment, the hearing assistance device (e.g. the analysis unit (ANA)) comprises a voice activity detector (VAD). A voice detector can be based on one or more of the electric input signals AIN, SIN1 and SIN2. Examples of voice detector circuits are e.g. described in WO 91/03042 A1 and in US 2002/0147580 A1. A voice detector can e.g. be used to enable a separation of signal and noise, allowing a signal to noise ratio (SNR) to be estimated as a function of time (and frequency if the signal is analysed in the time-frequency domain). A signal to noise ratio (SNR) estimated as a function of time and frequency (and a predefined criterion regarding relevant SNR-thresholds (e.g. frequency dependent)) can e.g. be used to select the time-frequency units to be used by the weighting unit (WGT) to form the resulting audio input signal IN.

In an embodiment, the hearing assistance device (e.g. the analysis unit (ANA) or a separate detector (DET)) comprises an own voice detector for detecting whether a given input sound (e.g. a voice) originates from the voice of the user of the system. In an embodiment, the microphone system of the hearing assistance device is adapted to be able to differentiate between a user's own voice and another person's voice and possibly NON-voice sounds. Own voice detection can e.g. be based on analysis of the electric input signal based on air conduction vibrations picked up by an 'ordinary' microphone. Alternatively (or additionally), own voice detection can be based on bone vibrations as e.g. picked up by a vibration sensing bone conduction microphone. Aspects of own voice detection are e.g. described in WO 2004/077090 A1 and in EP 1 956 589 A1.

In an embodiment, the hearing assistance device (e.g. the analysis unit (ANA)) comprises a feedback detector for detecting whether a given oscillation detected in the forward path of the device has its origin in an external signal or is due to feedback from the output transducer. In the embodiments of FIG. 3, the forward path includes resulting input signal IN, the processing unit (PRO), and processed (audio) output signal OUT. An example of a feedback detector is described in U.S. Pat. No. 7,925,031B2. In case it is concluded that substantial feedback is present in the electric input signal IN being processed by the signal processing unit to provide the processed output signal OUT (which in a NORMAL mode of operation is the audio input signal (AIN)), the hearing assistance device is brought into a FEEDBACK mode where the electric input signal IN is chosen to be one of (a weighted combination of) the supplementary input signals SIN1, SIN2, or a weighted combination of all three electric input signals SIN1, SIN2, AIN (cf. control signal C1), e.g. in a time-frequency representation (where feedback detection is performed on a time-frequency unit basis).

In an embodiment, the hearing assistance device (e.g. the detector unit (DET)) comprises a movement sensor (e.g. based on an acceleration and/or a gyroscope sensor). In an embodiment, the hearing assistance device (e.g. the detector unit (DET)) comprises a magnetic field sensor, (e.g. forming part of a GMR switch, GMR=Giant MagnetoResistance) for sensing the proximity of a (e.g. static or varying) magnetic field (e.g. a static field from a permanent magnet of a telephone device). In an embodiment, the hearing assistance device (e.g. the detector unit (DET)) comprises a detector indicating a state of the user (e.g. a temperature sensor, a brain wave sensor, a body sound detector, etc.). Such sensors can e.g. be included to improve the control of the composition of the resulting input audio signal IN (provided by the weighting unit (WGT)) and its processing (applied to the in the resulting input audio signal in the processing unit (PRO)).

Figure 4A:
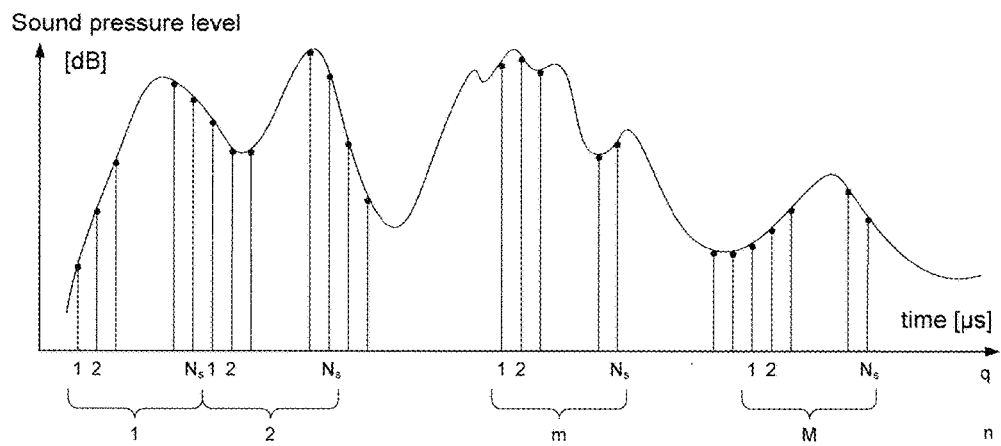
Figure 4B:
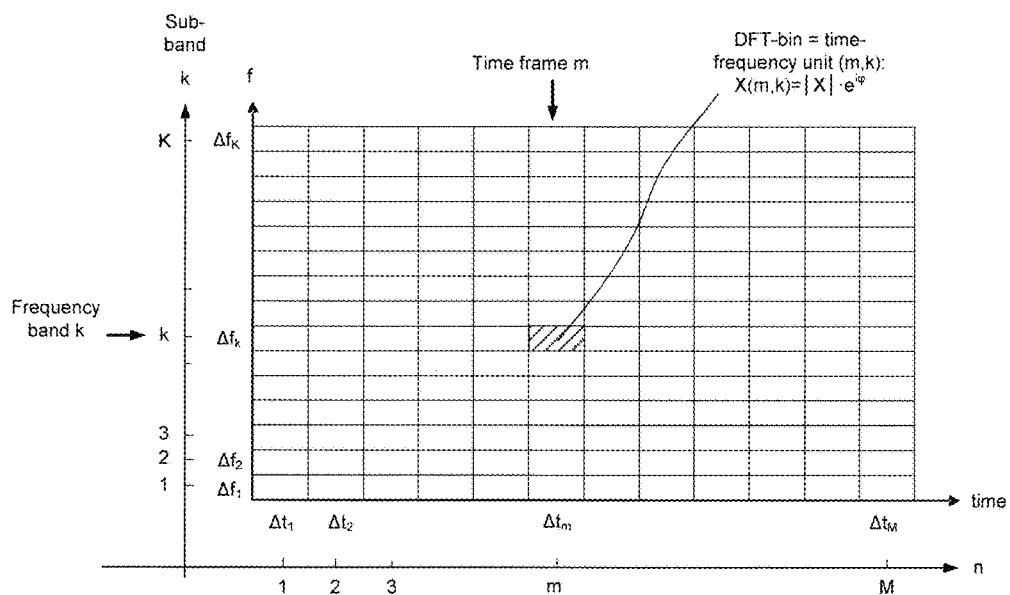

FIGS. 4A and 4B schematically show a conversion of a signal in the time domain to the time-frequency domain, FIG. 4A illustrating a time dependent sound signal (amplitude versus time) and its sampling in an analogue to digital converter, FIG. 4B illustrating a resulting 'map' of time-frequency units after a Fourier transformation of the sampled signal.

In an embodiment, the hearing assistance devices comprise an analogue-to-digital (AD) converter to digitize an analogue input with a predefined sampling rate, e.g. 20 kHz. In an embodiment, the hearing assistance devices comprise a digital-to-analogue (DA) converter to convert a digital signal to an analogue output signal, e.g. for being presented to a user via an output transducer.

In a typical hearing assistance device, an analogue electric signal representing an acoustic signal (as e.g. picked up by an input transducer, e.g. a microphone) is converted to a digital audio signal in an analogue-to-digital (AD) conversion process, where the analogue signal is sampled with a predefined sampling frequency or rate $f_s$, $f_s$ being e.g. in the range from 8 kHz to 50 kHz (adapted to the particular needs of the application) to provide digital samples $x_n$ (or x[n]) at discrete points in time $t_n$ (or n), each audio sample representing the value of the acoustic signal at $t_n$ by a predefined number $N_s$ of bits, $N_s$ being e.g. in the range from 1 to 16 bits. A digital sample x has a length in time of $1/f_s$, e.g. 50 μs, for $f_s$=20 kHz. In an embodiment, a number of audio samples are arranged in a time frame. In an embodiment, a time frame comprises 64 audio data samples. Other frame lengths may be used depending on the practical application.

In an embodiment, the hearing assistance device, e.g. the microphone unit, and or the transceiver unit comprise(s) a TF-conversion unit for providing a time-frequency representation of an input signal. In an embodiment, the time-frequency representation comprises an array or map of corresponding complex or real values of the signal in question in a particular time and frequency range. In an embodiment, the TF conversion unit comprises a filter bank for filtering a (time varying) input signal and providing a number of (time varying) output signals each comprising a distinct frequency range of the input signal. In an embodiment, the TF conversion unit comprises a Fourier transformation unit for converting a time variant input signal to a (time variant) signal in the frequency domain. In an embodiment, the frequency range considered by the hearing assistance device from a minimum frequency $f_{min}$ to a maximum frequency $f_{max}$ comprises a part of the typical human audible frequency range from 20 Hz to 20 kHz, e.g. a part of the range from 20 Hz to 12 kHz. In an embodiment, a signal of the forward and/or analysis path of the hearing assistance device is split into a number NI of frequency bands, where NI is e.g. larger than 5, such as larger than 10, such as larger than 50, such as larger than 100, such as larger than 500, at least some of which are processed individually. In an embodiment, the hearing assistance device is/are adapted to process a signal of the forward and/or analysis path in a number NP of different frequency channels (NP NI). The frequency channels may be uniform or non-uniform in width (e.g. increasing in width with frequency), overlapping or non-overlapping.

FIG. 4A schematically illustrates a time dependent sound signal (amplitude versus time), its sampling in an analogue to digital converter and a grouping of time samples in frames, each comprising $N_s$ samples. The graph showing a sound pressure level in dB versus time (solid line in FIG. 4A) may e.g. represent the time variant analogue electric signal provided by an input transducer, e.g. a microphone, before being digitized by an analogue to digital conversion unit. FIG. 4B illustrates a 'map' of time-frequency units resulting from a Fourier transformation (e.g. a discrete Fourier transform, DFT) of the input signal of FIG. 4A, where a given time-frequency unit (m,k) corresponds to one DFT-bin and comprises a complex value of the signal X(m,k) in question (X(m,k)=|X| ·$e^{i\varphi}$, |X|=magnitude and $\varphi$=phase) in a given time frame m and frequency band k. In the following, a given frequency band is assumed to contain one (generally complex) value of the signal in each time frame. It may alternatively comprise more than one value. The terms 'frequency range' and 'frequency band' are used in the present disclosure. A frequency range may comprise one or more frequency bands. The Time-frequency map of FIG. 4B illustrates time frequency units (m,k) for k=1, 2, . . . , K frequency bands and m=1, 2, . . . , M time units. Each frequency band $\Delta f_k$ is indicated in FIG. 4B to be of uniform width. This need not be the case though. The frequency bands may be of different width (or alternatively, frequency channels may be defined which contain a different number of uniform frequency bands, e.g. the number of frequency bands of a given frequency channel increasing with increasing frequency, the lowest frequency channel(s) comprising e.g. a single frequency band). The time intervals $\Delta t_m$ (time unit) of the individual time-frequency bins are indicated in FIG. 4B to be of equal size. This need not be the case though, although it is assumed in the present embodiments. A time unit $\Delta t_m$ is typically equal to the number $N_s$ of samples in a time frame (cf. FIG. 4A) times the length in time $t_s$ of a sample ($t_s$=(1/$f_s$), where $f_s$ is a sampling frequency, e.g. 20 kHz). A time unit is e.g. of the order of ms in an audio processing system.

FIG. 5 shows two embodiments of a hearing assistance device according to an aspect of the present disclosure adapted for being arranged at least partly on a user's head. The hearing assistance device may be partitioned and may comprise the functional elements as discussed in connection with FIG. 1-3 above. In the embodiment of FIG. 5, the hearing assistance device comprises a BTE part (BTE) adapted for being located behind an ear (pinna) of a user. The hearing assistance device further comprises output transducer (OT), e.g. a receiver/loudspeaker, adapted for being located in an ear canal of the user and (audio) input transducer (AIT), e.g. a microphone, adapted for being located at or in the ear canal of the user (e.g. but not necessarily forming part of the same physical body, e.g. a RITE-, or RIC- (Receiver-In-Canal) type hearing assistance device. The BTE-part is operationally connected to the output transducer (OT) and to the audio input transducer (AIT).

Figure 5A:
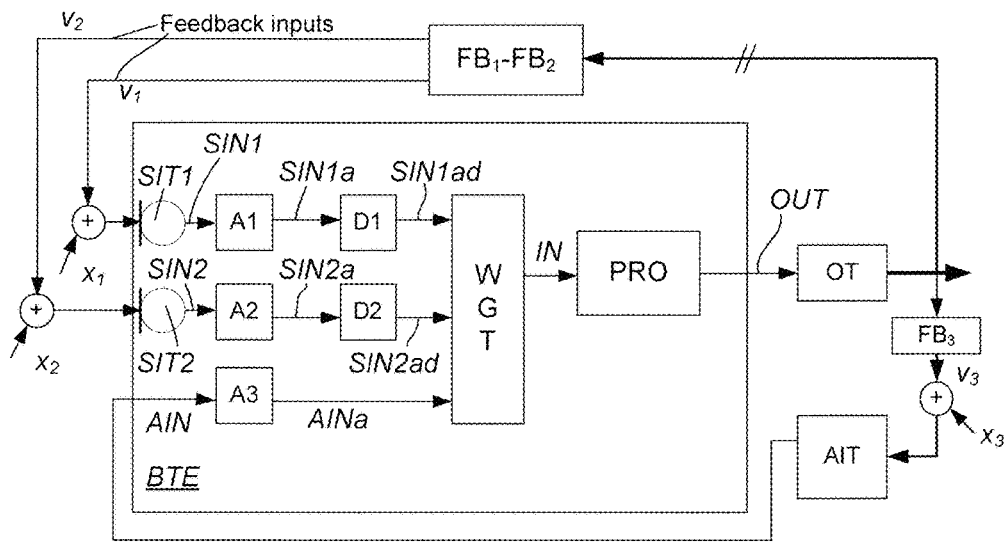
FIGS. 5A and 5B show two further embodiments of a hearing assistance device according to the present disclosure.

In the embodiment of FIG. 5A, the BTE-part comprises first and second supplementary input transducers (SIT1, SIT2), here microphones, providing first and second supplementary electric input signals SIN1, SIN2. Each input transducer path comprises an amplifier for selectively amplifying the electric input signal. The supplementary input transducers (SIT1, SIT2) are connected to respective first and second amplification unit, A1, A2 providing first and second amplified input signals SIN1a, SIN2a. The audio input transducer is connected to (third) amplifier unit A3 providing amplified input signal AINa. The first and second amplification units, A1, A2 are connected to respective first and second delay units D1, D2 for selectively applying delay to the respective input signals and providing respective delayed input signals SIN1ad, SIN2ad. Delayed input signals SIN1ad, SIN2ad and amplified input signal AINa are fed to weighting unit (WGT) for mixing two or all of the input signals (e.g. providing a weighted sum, e.g. adding them (weights=1)) or selecting one of the inputs and providing a resulting input signal IN that is fed to processing unit PRO for further enhancement (e.g. noise reduction, feedback suppression, etc.). The feedback paths from the output transducer (OT) to the respective input transducers SIT1, SIT2, AIT are denoted $FB_1$, $FB_2$ and $FB_3$, respectively, and the corresponding feedback signals reaching the input transducers are denoted $v_1$, $v_2$ and $v_3$, respectively. The feedback signals are mixed with respective signals $x_2$ and $x_3$, from the environment. In a normal situation (considering the location of the output transducer relative to the input transducers, the feedback signal $v_3$ at the audio input transducer will be far larger than the feedback signals $v_1$, $v_2$ arriving at the supplementary input transducers of the BTE part. The amplifier units A1, A2, A3 are hence configured to apply a larger amplification to electric input signals SIN1, SIN2 from (supplementary) input transducers (SIT1, SIT2) than to the electric audio input signal AIN (i.e. A1, A2>A3, e.g. A1, A2≥A3+20 dB, e.g. A1=A2) from the audio input transducer (AIT). The (supplementary) input transducers are e.g. arranged in the BTE-part to be located behind the pinna (e.g. at the top of pinna), whereas the (audio) input transducer is located in or around the entrance to the ear canal. The delay applied by delay units D1, D2 to the respective (amplified) signals SIN1a, SIN2a from the (supplementary) input transducers is preferably configured to be between 1 and 20 milliseconds (e.g. D1=D2). The size of the delay may e.g. be determined (e.g. during a fitting—try and error-procedure)

as the best compromise between sound quality aspects such as perceived acoustic echo and the correct perception of directionality of the sound.

Figure 5B:
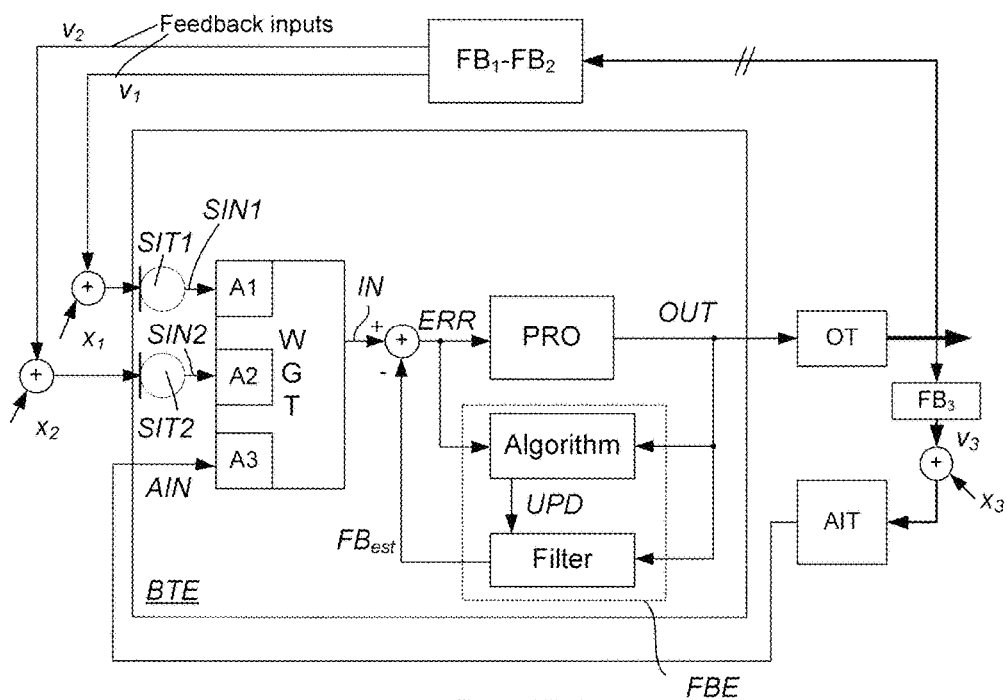
Figure 6A:
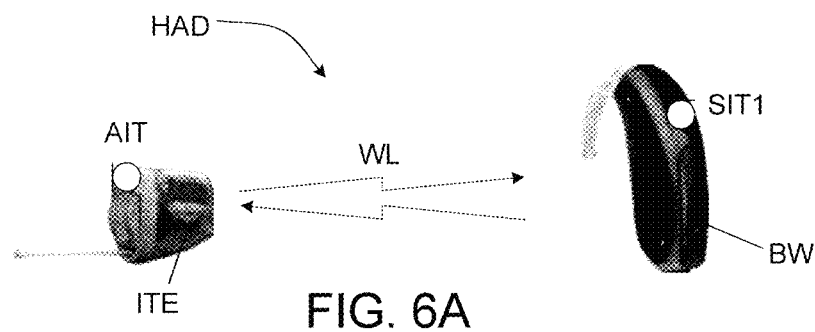
FIG. 6A, 6B, 6C, 6D show four exemplary configurations of a hearing assistance device according to the present disclosure.
Figure 6B:
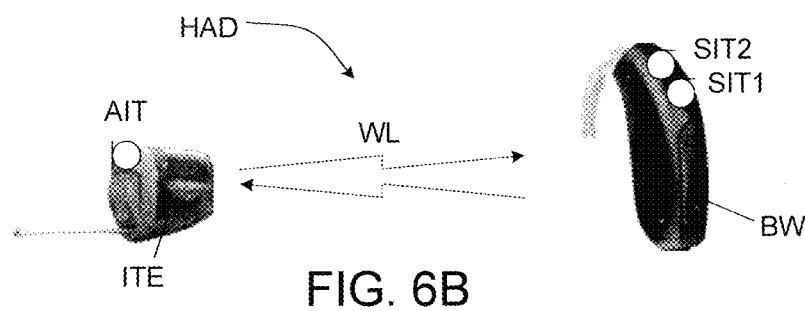
Figure 6C:
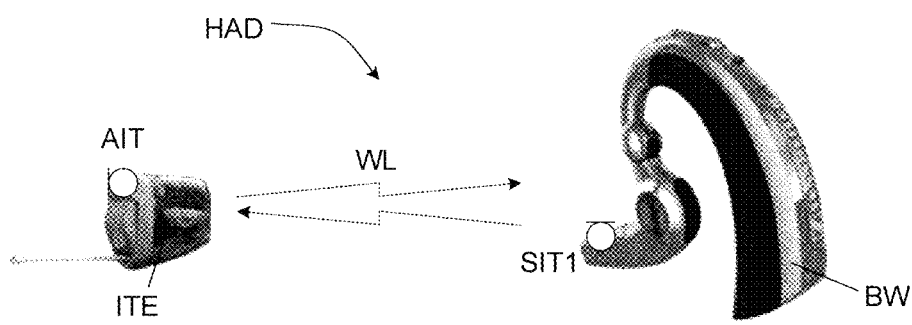
Figure 6D:
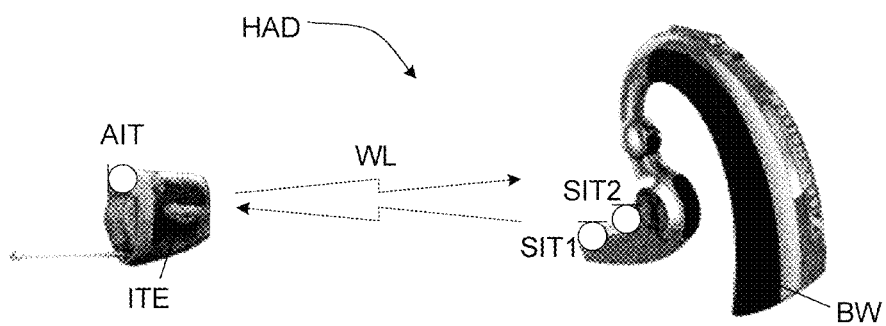

In the embodiment of FIG. 5B, the BTE-part comprises the same functional elements as shown and described in connection with FIG. 5A. The delay units D1 and D2 may form part of the (possibly) complex weighting performed in the weighting unit (WGT). In addition, the BTE-part of the embodiment of FIG. 5B comprises a feedback suppression system comprising a feedback estimation unit (FBE). The feedback estimation unit (FBE) comprises an adaptive filter comprising an adaptive algorithm part (Algorithm) for determining update filter coefficients, which are fed (signal UPD) and applied to a variable filter part (Filter) of the adaptive filter. The feedback suppression system further comprises a combination unit (+) wherein an estimate of the current feedback path FBest is subtracted from the resulting input signal IN from the weighting unit (WGT) and the resulting (feedback reduced) 'error' signal ERR is fed to the signal processing unit (PRO) for further processing and to the algorithm part of the adaptive filter for use in the estimation of the feedback path. The feedback estimation unit (FBE) provides the estimate FBest of the current feedback path based on the output signal OUT from the signal processing unit and the error signal ERR (in that the adaptive algorithm minimizes the error signal ERR given the current output signal OUT). In an embodiment, the hearing assistance device (e.g. the weighting unit (WGT)) comprises a feedback detector (e.g. an autocorrelation or a cross-correlation detector) to allow the hearing assistance device to identify feedback or build-up of feedback (risk of feedback), e.g. in the audio input signal AIN, and thereby to allow a proper reaction, e.g. to take a part of the audio input from the supplementary microphones. In an embodiment, each of the microphones (AIT, SIT1, SIT2) has its own feedback suppression system.

Example

A modular hearing aid concept comprising an autonomous (e.g. very discreet) instant in-ear device and an auxiliary (optional) unit, e.g. configured to be located behind the ear, is proposed. The in-ear part (ITE) preferably constitute the main hearing aid whereas the auxiliary unit (the BW- or BTE-part) is mounted when needed. The two parts are adapted to hook up via a wireless connection (e.g. a Bluetooth link, or preferably (for minimum power reasons), an inductive link) when the BW/BTE-part is mounted and e.g. speech enhancement is required. In this way a strong directionality effect can be obtained for meetings etc. and at the same time the user may use the discreet in-ear device most of the time. The BW-/BTE-part may also constitute the platform for Bluetooth communication (to other auxiliary devices, e.g. telephone, partner microphone, audio from a TV or the like). The BW-/BTE-part will typically be larger than the ITE-part and thus contain a larger power supply (battery) to better be able to support additional functionality (e.g. Bluetooth communication).

This concept is illustrated in FIG. 6, where a hearing assistance device HAD comprising an ITE part (e.g. being a functional hearing device in itself, cf. e.g. FIG. 1F), and a body-worn part (BW), here in the form of a BTE-part adapted for being located behind an ear of a user, is provided. The ITE- and BW-/BTE-parts are configured to establish a wireless link (WL) between them allowing data to be exchanged between the two devices, including the transmission of audio data from the BW-part to the ITE-part. Four embodiments of such system is illustrated in FIG. 6. In the embodiment illustrated in FIG. 6A, a (audio) microphone (AIT) of the ITE-part at the ear canal entrance is combined with a (supplementary) microphone (SIT1) behind the pinna when the BTE-part (BW) is operationally mounted. In the embodiment of FIG. 6B, an additional (supplementary) microphone (SIT2) is located in the BTE-part (BW) behind the pinna allowing for high frequency directionality between the two microphones behind pinna, while maintaining the option of low frequency directionality between one or both the microphones behind the ear and the microphone (AIT) of the ITE-part at the ear canal entrance. In the embodiment of FIG. 6C, the body-worn part is a headset (or headset-like hearing device), and the microphone (AIT) of the ITE-part at the ear canal entrance is combined with a microphone (SIT1) on a boom or similar in front of the pinna. This offers the possibility of directionality undisturbed by the influence of the pinna on the sound field and is also beneficial for the use of the device as a headset since it offers the possibility of optimizing the acoustic reception of speech from the wearers own mouth. In the embodiment of FIG. 6C, an additional microphone (SIT2) is added on the boom in front of the pinna for increased directionality and speech enhancement.

In all cases the connection between the signals from the microphones may be realized by wireless low power signal transmission such as made possible by near-field communication, e.g. an inductive link. In such case, a time delay in the order of 3 milliseconds may be introduced by the transmission system. This should be taken into consideration in the design and a similar delay be introduced in the signal path from the microphone directly attached to the part of the device containing the signal processor in order to properly time align the incoming audio signals before further treatment.

The BW-part may be used in combination with a CIC device (the ITE-part) having a small vent opening in order to minimize the risk of subjective disturbances from possible time delay between the audio signal emitted by the hearing assistance device receiver (loudspeaker) and the sound entering the ear canal directly through the vent opening.

The BW-part may be used in combination with a deeply inserted ear-canal part (the ITE-part) in order to minimize the risk of occlusion problems experienced by the end user and arising from the use of a small vent opening.

In an embodiment, the ITE-part located inside the ear canal (e.g. deep in the ear canal, e.g. in the bony part, is designed for low power consumption and contains only a small battery, being either rechargeable or interchangeable. In an embodiment, the ITE part is adapted for being dispensable.

The invention is defined by the features of the independent claim(s). Preferred embodiments are defined in the dependent claims. Any reference numerals in the claims are intended to be non-limiting for their scope.

Some preferred embodiments have been shown in the foregoing, but it should be stressed that the invention is not limited to these, but may be embodied in other ways within the subject-matter defined in the following claims and equivalents thereof. The illustrative examples of hearing assistance devices described above are largely described in the framework of an air conduction hearing instrument, where the input transducers are microphones and the output transducer is a receiver (loudspeaker). It might, however, as well be implemented as a bone conducting hearing device comprising an audio microphone located in the ear and one or more supplementary microphones located in another part of the device and wherein the output transducer comprises a vibrator for transferring vibrations to the skull of the user for being perceived by the user as sound. Alternatively, it might be a cochlear implant hearing device comprising an audio microphone located in the ear and one or more supplementary microphones located in another part of the device (e.g. behind the ear) and wherein the output transducer comprises an electrode for stimulating a hearing nerve in a user's cochlea to allow the user to perceive the stimulus as sound. Also hearing assistance devices comprising several output transducers (instead of only one as exemplified above) can be provided. For example, a hybrid hearing assistance device comprising a cochlear implant output transducer (electrode) and a loudspeaker for acoustically stimulating the eardrum of the user, can be implemented, the hybrid hearing assistance device comprising an audio microphone located in the ear of the user. Cochlear implant type hearing assistance devices are e.g. described in U.S. Pat. No. 4,207,441 and in U.S. Pat. No. 4,532,930.

REFERENCES

US2010150385A1 (SAT) 17 Jun. 2010
US2008107292A1 (SAT) 8 May 2008
U.S. Pat. No. 7,471,799B2 (OTICON) 24 Mar. 2005
[Schaub; 2008] Arthur Schaub, Digital hearing Aids, Thieme Medical. Pub. 2008.
[Haykin] S. Haykin, Adaptive filter theory (Fourth Edition), Prentice Hall, 2001.
[Engebretson, 1993] A. Engebretson, M. French-St. George, "Properties of an adaptive feedback equalization algorithm", J Rehabil Res Dev, 30(1), pp. 8-16, 1993
[Kjems and Jensen; 2012] Ulrik Kjems, Jesper Jensen, "Maximum likelihood based noise covariance matrix estimation for multi-microphone speech enhancement", 20th European Signal Processing Conference (EUSIPCO 2012), Bucharest, Romania, August 27-31, 2012, pp. 296-299.
EP1448016A1 (OTICON) 18 Aug. 2004
EP2088802A1 (OTICON) 12 Aug. 2009
WO 03/081947 A1 (OTICON) 2 Oct. 2003
U.S. Pat. No. 5,144,675 (ETYMOTIC) 1 Sep. 1992
WO 91/03042 A1 (OTWIDAN) 7 Mar. 1991
US 2002/0147580 A1 (ERICSSON) 10 Oct. 2002
U.S. Pat. No. 7,925,031B2 (OTICON) 30 Nov. 2006
U.S. Pat. No. 4,207,441 (BERTIN & CIE) 10 Jun. 1980
U.S. Pat. No. 4,532,930 (COMMONWEALTH OF AUSTRALIA) 6 Aug. 1985.

The invention claimed is:

1. A hearing assistance device adapted for being arranged at least partly on a user's head or at least partly implanted in a user's head, the hearing assistance device comprising:
an input transducer system comprising
an audio input transducer for picking up a sound signal from the environment and providing an electric audio input signal,
a first and second supplementary input transducer for picking up a sound signal from the environment and providing a first and second supplementary electric input signal,
an output transducer for converting a processed output signal to a stimulus perceivable by said user as sound,
a time to time-frequency conversion unit allowing a signal to be processed or analyzed at different frequencies;
one or more detectors of the acoustic environment of the hearing assistance device selected among a group consisting of a wind noise detector, a voice activity detector, an own voice detector, a feedback or howl or loop gain detector, an autocorrelation or cross-correlation detector, a level detector, and a proximity detector, and
a signal processing unit operationally connected to said audio input transducer, to said first and second supplementary input transducer, and to said output transducer, said signal processing unit being configured for processing said electric audio input signal, and said first and second supplementary electric input signal, and for providing said processed output signal, wherein the signal processing unit is configured to provide that said processed output signal is a mixture according to a predefined scheme of said electric audio input signal said first and second supplementary electric input signals on a time frequency unit basis, and wherein the actual mixture is influenced by said one or more detectors, and
wherein said audio input transducer is adapted for being located in an ear of said user.

2. A hearing assistance device according to claim 1, wherein the signal processing unit is configured to provide that said processed output signal, in a normal mode of operation of the hearing assistance device, originates from said electric audio input signal.

3. A hearing assistance device according to claim 1 wherein the audio input transducer is located in the conchae, or at the entrance to the ear canal, or in the ear canal.

4. A hearing assistance device according to claim 1 wherein the output transducer comprises a receiver for converting said output signal to an acoustic sound signal.

5. A hearing assistance device according to claim 1 wherein the audio input transducer is located in an ITE-part of the hearing assistance device, where the ITE-part is adapted for being located at least partially in an ear canal of the user.

6. A hearing assistance device according to claim 1 wherein the signal processing unit is located in a body-worn part adapted for being located at said user.

7. A hearing assistance device according to claim 1 wherein the body-worn part and the ITE-part are two separate bodies, and wherein a connecting element provides at least mechanical connection between the two parts.

8. A hearing assistance device according to claim 7 wherein the body-worn part comprises or is constituted by a behind-the-ear (BTE) part adapted for being worn behind an ear (pinna) of the user.

9. A hearing assistance device according to claim 1 wherein at least one of the supplementary input transducer(s) form part of said one or more detectors.

10. A hearing assistance device according to claim 1 comprising a weighting unit providing a directional output signal from a number of input signals wherein said number of input signals comprise said electric audio input signal and said first and second and optionally further supplementary electric input signals.

11. A hearing assistance device according to claim 1 comprising a howl detector for detecting the occurrence or build-up of feedback howl, and wherein the signal processing unit is configured to provide that said processed output signal, in a feedback mode of operation of the hearing assistance device where feedback howl build-up of feedback howl is detected, originates from said first and second and optionally further supplementary electric input signals.

12. A hearing assistance device according to claim 8 wherein the first and second supplementary input transducers comprise microphones and are located on the top of the BTE-part, whereby the sounds from front and rear directions relative to the user can be received by the microphones.

13. A hearing assistance device according to claim 1 wherein the predefined scheme comprises selecting the time frequency units having the largest signal to noise ratio among corresponding time frequency units of the electric input signals.

14. A hearing assistance device according to claim 1 wherein frequency bands dominated by unwanted sounds are identified by the supplementary input transducer(s), and wherein a resulting supplementary control signal is used in the processing of the audio signal.

15. A hearing assistance device according to claim 1 wherein a supplementary input transducer is configured to identify noise in the environment.

16. A hearing assistance device according to claim 1 configured to reduce gain in the processing of the audio input signal when only noise is present and to increase gain when speech (and noise) is present.

17. A hearing assistance device according to claim 1 wherein a supplementary input transducer is configured to identify wind noise and to remove (or attenuate) such low-frequency noise in the audio input signal.

18. A hearing assistance device according to claim 1 wherein the supplementary input transducer is configured to identify a user's own voice.

19. A hearing assistance device according to claim 1 wherein the signal, or one or more frequency bands thereof, from one supplementary input transducer or from a weighted combination of several supplementary input transducers is, in a particular feedback mode of operation, fully or partially used as the audio signal in case of howling due to feedback problems in the hearing assistance device.

20. A hearing assistance device according to claim 1 wherein said hearing assistance device is part of a hearing aid, a headset, an earphone, or an ear protection device.

* * * * *